(12) United States Patent
Gallagher

(10) Patent No.: US 7,277,527 B2
(45) Date of Patent: Oct. 2, 2007

(54) MOVEABLE TRANSPARENT BARRIER FOR X-RAY ANALYSIS OF A PRESSURIZED SAMPLE

(75) Inventor: Brian Gallagher, Guilderland, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 134 days.

(21) Appl. No.: 11/300,909

(22) Filed: Dec. 15, 2005

(65) Prior Publication Data

US 2006/0093086 A1 May 4, 2006

Related U.S. Application Data

(63) Continuation of application No. PCT/US2004/019256, filed on Jun. 16, 2004.

(60) Provisional application No. 60/479,035, filed on Jun. 17, 2003.

(51) Int. Cl.
*H01J 35/12* (2006.01)
*H01J 35/10* (2006.01)
*H01J 35/00* (2006.01)

(52) U.S. Cl. .................. 378/141; 378/193; 378/47; 378/137; 250/432 R

(58) Field of Classification Search .......... 378/45, 378/46, 44, 57, 82, 141; 250/432 R
See application file for complete search history.

(56) References Cited

U.S. PATENT DOCUMENTS 3,557,376 A   1/1971  Senyk et al. ............. 250/218
3,838,924 A   10/1974 Flower et al. ............ 356/28
5,236,326 A * 8/1993  Grossa .................. 425/174.4
2003/0228475 A1* 12/2003 Komada ................. 428/447
2004/0105981 A1*  6/2004 Yializis ................. 428/421
2004/0229394 A1* 11/2004 Yamada et al. ........... 438/66
2005/0249898 A1* 11/2005 Komada et al. ......... 428/35.2
2007/0020451 A1*  1/2007 Padiyath et al. ......... 428/336
2007/0031703 A1*  2/2007 Komada et al. ......... 428/702

FOREIGN PATENT DOCUMENTS

FR   2212931 A   7/1974
GB   1066351 A   4/1967
JP   62 043542 A  2/1987

* cited by examiner

*Primary Examiner*—Robert Kim
*Assistant Examiner*—Johnnie L Smith, II
(74) *Attorney, Agent, or Firm*—Jeffrey R. Klembczyk, Esq.; Kevin P. Radigan, Esq.; Heslin Rothenberg Farley & Mesiti, P.C.

(57) ABSTRACT

A technique is disclosed for presenting a sample to a radiation interface of an analysis engine employing x-ray, neutron ray, gamma ray or particle-beam radiation to analyze the sample. A protective barrier, transparent to the radiation, and separating the sample from the engine, is moveable relative to the radiation interface, using a barrier movement system. The barrier in one embodiment is a film movable over a cavity in which the sample placed, and moveable with a system of reels to provide and retrieve a generally continuous supply of film over the cavity. The cavity may form a portion of a sample path through which the sample is moveable. If the sample path is pressurized, the film maintains the pressure during analysis of the sample by the analysis engine.

36 Claims, 10 Drawing Sheets

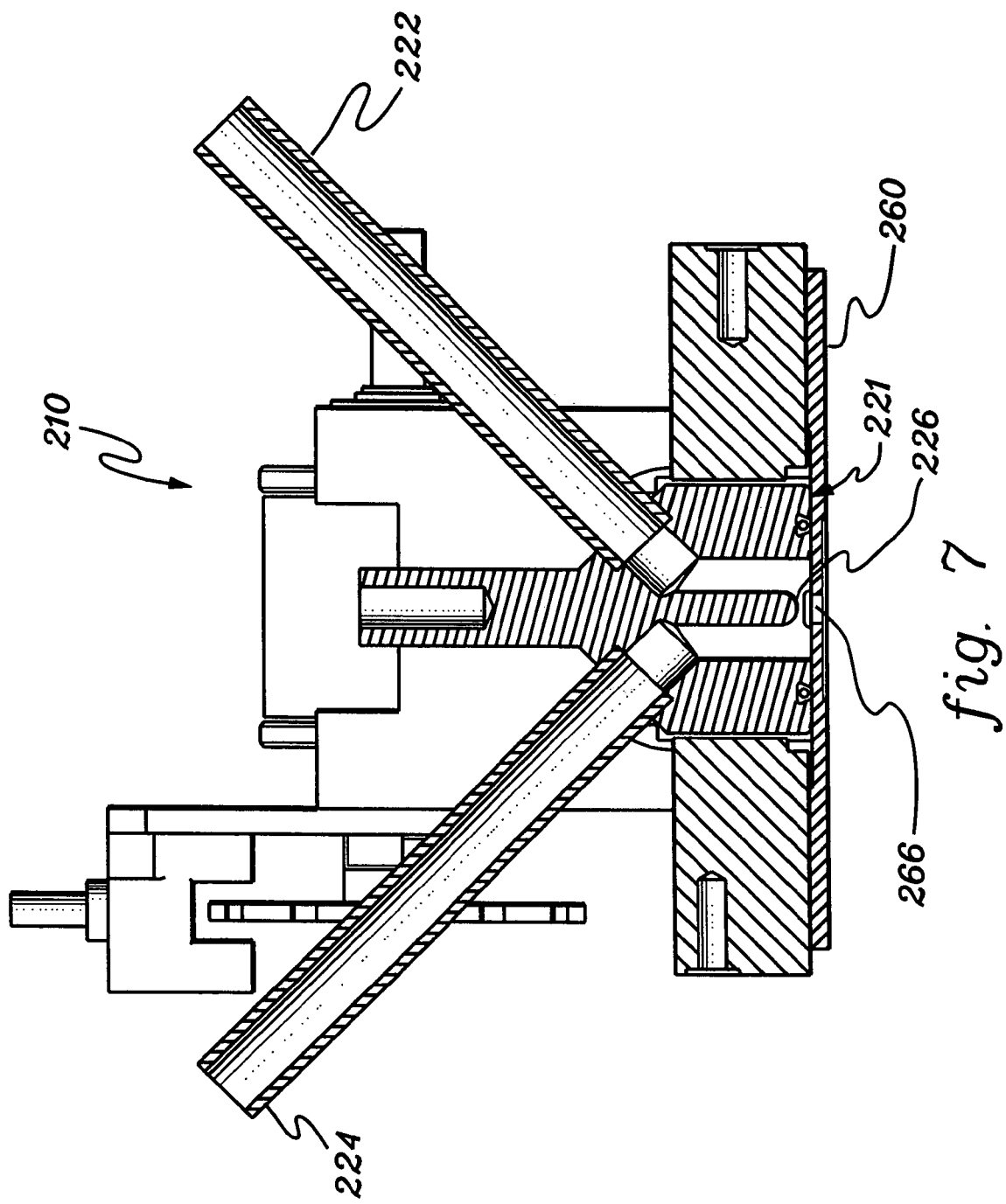

US 7,277,527 B2

MOVEABLE TRANSPARENT BARRIER FOR X-RAY ANALYSIS OF A PRESSURIZED SAMPLE

CROSS-REFERENCE TO RELATED APPLICATIONS

This application is a continuation of PCT Application PCT/US2004/019256 filed Jun. 16, 2004, and published under the PCT Articles in English as WO 2004/113894 A1 on Dec. 29, 2004. PCT/US2004/019256 claimed priority to U.S. Provisional Application No. 60/479,035, filed Jun. 17, 2003. The entire disclosures of PCT/US2004/019256 and U.S. Ser. No. 60/479,035 are incorporated herein by reference in their entirety. In addition, this application contains subject matter which is related to the subject matter of the following applications, which are hereby incorporated herein by reference in their entirety:

"XRF SYSTEM INCLUDING FOCUSING OPTIC ON EXCITATION SIDE AND MONOCHROMATIC COLLECTION" by Chen, et al. U.S. Ser. No. 60/299,371 filed Jun. 19, 2001;

"X-RAY TUBE AND METHOD AND APPARATUS FOR ANALYZING FLUID STREAMS USING X-RAYS" by Radley, et al. U.S. Ser. No. 60/336,584 filed Dec. 4, 2001;

"A METHOD AND APPARATUS FOR DIRECTING X-RAYS" by Radley, U.S. Ser. No. 60/383,990 filed May 29, 2002;

"X-RAY SOURCE ASSEMBLY HAVING ENHANCED OUTPUT STABILITY" by Radley, et al., U.S. Ser. No. 60/398,965 filed Jul. 26, 2002;

"METHOD AND DEVICE FOR COOLING AND ELECTRICALLY INSULATING A HIGH-VOLTAGE, HEAT-GENERATING COMPONENT" by Radley, U.S. Ser. No. 60/398,968 filed Jul. 26, 2002;

"AN ELECTRICAL CONNECTOR, A CABLE SLEEVE, AND A METHOD FOR FABRICATING AN ELECTRICAL CONNECTION" by Radley, U.S. Ser. No. 10/206,531 filed Jul. 26, 2002;

"DIAGNOSING SYSTEM FOR AN X-RAY SOURCE ASSEMBLY" by Radley, et al., U.S. Ser. No. 60/398,966 filed Jul. 26, 2002; and "MOVEABLE TRANSPARENT BARRIER FOR X-RAY ANALYSIS OF A PRESSURIZED SAMPLE" by Gallagher, U.S. Ser. No. 60/479,035, filed Jun. 17, 2003;

TECHNICAL FIELD

This invention relates generally to apparatus and methods used for x-ray analysis of sample materials. More particularly, the present invention provides a moveable, protective, x-ray-transparent barrier between an x-ray source/detector assembly and a sample material.

BACKGROUND OF THE INVENTION

As discussed in the above-incorporated U.S. patent applications, x-ray analysis methods provide some of the most significant developments in twentieth and twenty-first century science and technology. The use of x-ray fluorescence, x-ray diffraction, x-ray spectroscopy, x-ray imaging, and other x-ray analysis techniques has led to a profound increase in knowledge in virtually all scientific fields.

X-ray fluorescence (XRF) is an analytical technique by which a substance is exposed to a beam of x-rays to determine, for example, the presence of certain components. In XRF, at least some of the chemical constituents of the substance exposed to x-rays can absorb x-ray photons and produce characteristic secondary fluorescence. These secondary x-rays are characteristic of the chemical constituents in the substance. Upon appropriate detection and analysis these secondary x-rays can be used to characterize one or more of the chemical constituents. XRF techniques have broad applications in many chemical and material science fields, including medical analysis, semiconductor chip evaluation, and forensics, among others.

One emerging application for such measurement techniques is the detection of sulfur in fuels. Sulfur in transportation fuels is emitted as $SO_2$ or $SO_3$, which typically forms sulfuric acid in the atmosphere, and some of which forms ammonium sulfate or ammonium bisulfate. These sulfur compounds are the dominant contributor to PM 2.5 pollution. Although there are other human-based sources of sulfur, transportation fuels have been a major contributor. In New York City more than half the sulfur in air pollution is attributable to transportation sources. Sulfur in fuels poisons catalytic converters, and reductions in sulfur levels in fuels also reduce other pollutants from transportation sources. To address these problems, the U.S. Environmental Protection Agency (EPA) has recently mandated a reduction of sulfur in on-road diesel fuel from the current level of 500 ppm to 15 ppm by 2006. The EPA estimates that the rule will annually prevent over 8,000 premature deaths and tens of thousands of cases of bronchitis and asthma in the U.S. Europe and Japan are making similar changes in approximately the same time frame.

The petroleum industry has demonstrated the ability to remove sulfur from highway fuels. However, controlling fuel production and distribution are problematic, as there are no robust methods for on-line measurement of sulfur level in fuels during their processing and distribution. To meet the 15 ppm mandated levels, approximately 7-8 ppm must be measured at refineries to account for contamination during transportation. To attain good statistical control and to monitor feedstocks with lower than average sulfur levels, the limit of detection may need to be less than 1 ppm.

XRF techniques can be used for this application (as discussed above and throughout the above-incorporated applications). The basic technique involves exciting a fuel sample with x-rays and examining the fluorescence emitted. Each element emits a unique spectral signature. A detector then measures the wavelengths of the emitted x-rays, and software can reduce this measured spectrum to a weighted composition of the sulfur in the sample.

XRF fluid testing can take place off-line, i.e., using a bench-top, laboratory-type instrument to analyze a sample. The material is removed from its source (e.g., for fuel, from a refinery or transportation pipeline) and then simply deposited in a sample chamber. Off-line instruments need not meet any unusual operational/pressure/environmental/size/weight/space/safety constraints, but merely need to provide the requisite measurement precision for a manually-placed sample. Moreover, off-line instruments can be easily maintained between measurements.

On-line analysis offers the potential of "real-time" monitoring of sample composition at various points in the manufacturing process. For example, all fuel product is subject to the EPA rules discussed above—requiring some variant of on-line monitoring during fuel refining and transportation in pipelines. On-line analysis of fuels in a refinery and in pipelines, however, requires consideration of numerous operational issues not generally present in an off-line, laboratory setting. A fully automated fuel sample handling system is required—with little or no manual intervention or maintenance. Also, since fluids are usually under pressure in pipelines, any sample handling system must account for pressure differentials. This is especially important since certain portions of XRF x-ray "engines" (discussed further below) may operate in a vacuum. Also, the instrument's electronics require packaging in an explosion-proof housing—separate from the sample handling system.

In this application, therefore, one of the most critical components is the sample barrier which allows photons of x-rays to excite sulfur atoms in the fluid, and photons emitted from the atoms to be counted at the engine's detector, while at the same time maintaining the vacuum or atmosphere in the x-ray engine and the pressure of the fluid. The present inventors have discovered that x-ray stimulation creates sulfur ionization and adsorption at this interface over time and on certain types of barrier materials—leading to undesired sulfur residue and degradation of the barrier's x-ray transparency. More generally, many XRF applications require a barrier to protect the engine from any number of adverse interface effects from the sample material and/or the measurement environment.

Therefore, any barrier technique in an on-line system should meet certain criteria: transparency—i.e., the transmission of x-rays with the minimum amount of x-ray absorption; strength—the barrier material must be strong enough to support, e.g., fluid sample pressures of 20-100 psi or more from continuous flows in a pipeline; and finally, contamination—the technique must address contamination of the barrier from the sample material and/or the measurement environment.

What is required, therefore, is a barrier technique and apparatus for an on-line x-ray analysis system, which protects the x-ray engine from adverse sample and environmental effects, while maintaining the integrity and transparency of the interface to the sample for accurate measurements.

SUMMARY OF THE INVENTION

The present invention provides a technique, including methods and apparatuses, which together address these problems. A technique is disclosed for presenting a sample to a radiation interface of an analysis engine employing x-ray, neutron ray, gamma ray or particle-beam radiation to analyze the sample. A barrier, transparent to the radiation, and separating the sample from the engine, is moveable relative to the radiation interface, using a barrier movement system. The barrier in one embodiment is a film movable over a cavity in which the sample placed, and moveable with a system of reels to provide and retrieve a generally continuous supply of film over the cavity.

The cavity may form a portion of a sample path through which the sample is moveable. If the sample path is pressurized, the film maintains the pressure during analysis of the sample by the analysis engine.

As discussed above, when the sample is a liquid, the sample path comprises at least a portion of a pressurized pipeline through which the liquid is flowing, and the analysis engine performs a compositional analysis of the fluid while the fluid is flowing. In one embodiment, a sample chamber assembly may be provided having a surface into which the sample cavity is formed, along with a plate opposing the sample cavity having an aperture allowing passage of the radiation to and from the sample cavity. The film is disposed between the surface of the sample chamber and the plate, and the sample chamber is moveable relative to the plate to increase and decrease pressure on the film. The apparatus may comprise a spring or other pressure-applying device to apply consistent pressure on the o-ring when the film is being moved; the plate may comprise a coating to reduce friction between the plate and the film; and the sample cavity may be sized to reduce background scatter.

These and other embodiments and aspects of the present invention will become more apparent upon review of the attached drawings, description below, and attached claims.

BRIEF DESCRIPTION OF THE DRAWINGS

The subject matter regarded as the invention is particularly pointed out and distinctly claimed in the concluding portion of the specification. The invention, however, both as to organization and method of practice, together with further objects and advantages thereof, may best be understood by reference to the following detailed descriptions of the preferred embodiments and the accompanying drawings in which:

FIG. 7 is a sectional view of the apparatus of FIGS. 3-5 taken along section BB.

DETAILED DESCRIPTION OF THE PREFERRED EMBODIMENTS

Figure 1:
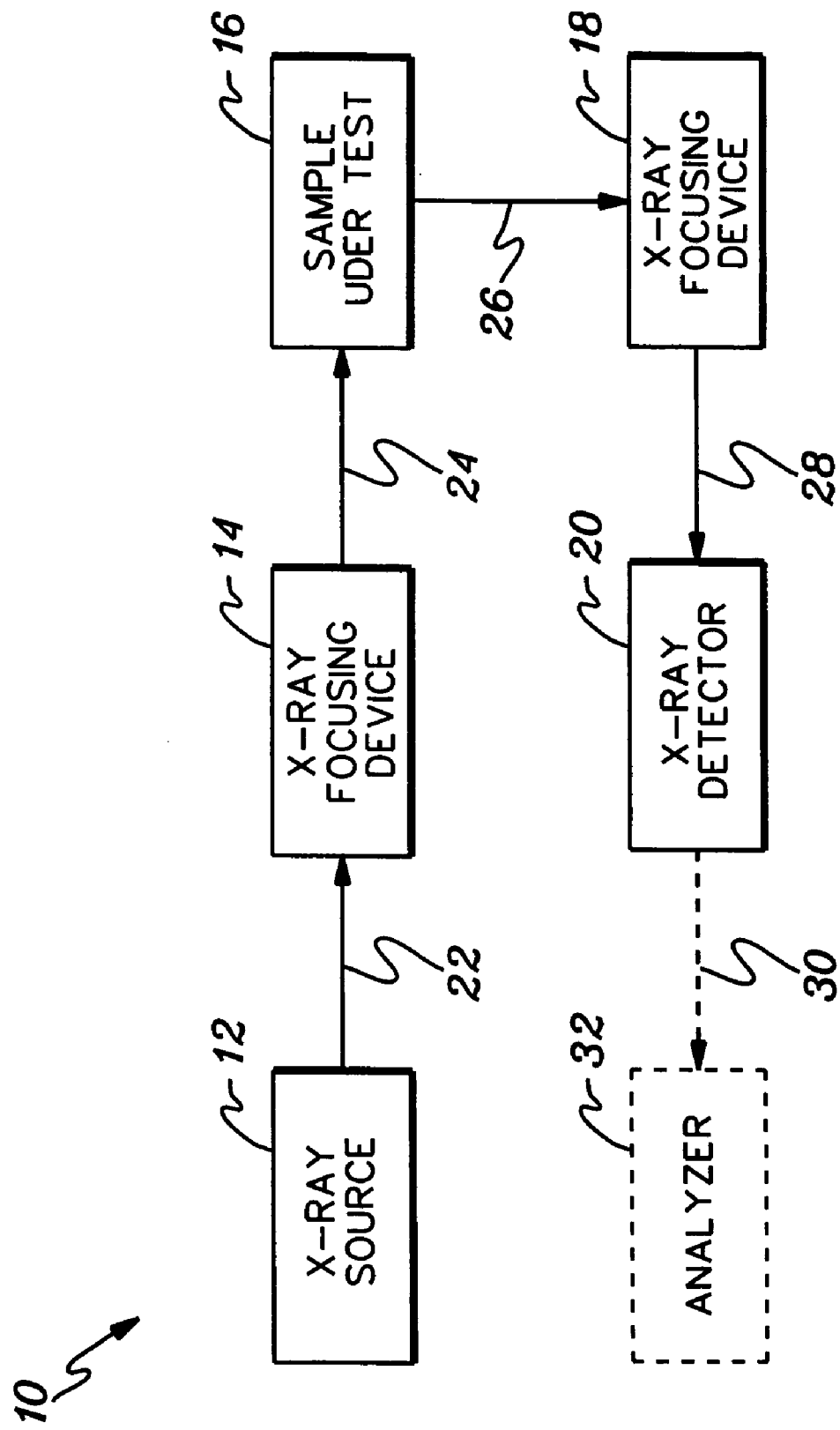
FIG. 1 is a schematic block diagram of an x-ray fluorescence system.

FIG. 1 is a schematic block diagram of a typical system 10 used for exposing a substance to x-ray radiation to produce fluorescent radiation which can then be detected and analyzed to determine a characteristic of the substance. The system typically includes an x-ray source 12, a first x-ray focusing device 14, a sample excitation chamber 16, a second x-ray focusing device 18, and an x-ray detector 20. The x-ray source 12, for example, an x-ray tube, produces a beam of x-rays 22. Though x-rays are used throughout the specification, the invention extends to neutron, particle-beam or gamma ray radiation Since x-ray beam 22 is typically a divergent beam, beam 22 is diffracted or focused by means of one or more x-ray focusing devices 14. X-ray focusing device 14 may be one or more doubly-curved crystals, for example, a doubly-curved crystal having essentially parallel atomic planes, such as the crystals disclosed in pending app. Ser. No. 09/667,966 filed on Sep. 22, 2000 (Atty. Ref. 0444.035), the disclosure of which is incorporated by reference herein. X-ray focusing device may be one or more capillary-type x-ray optic or curved crystal optic or multilayer optic, for example, one of the optics disclosed in U.S. Pat. Nos. 6,317,483; 6,285,506; 5,747,821; 5,745,547; 5,604,353; 5,570,408; 5,553,105; 5,497,008; 5,192,869; and 5,175,755, the disclosures of which are incorporated by reference herein. The x-ray focusing device produces a focused beam 24 directed toward the sample excitation chamber 16.

The sample under test in excitation chamber 16 may be any desired substance for which a characteristic is desired. If the sample is static (in, for example, an off-line system), the sample is typically located on a relatively flat surface, for example, an x-ray reflective flat surface or an optically-reflective surface. The sample, if a solid, liquid, or gas, may also be contained in a closed container or chamber, for example, a sealed container, having a x-ray transparent aperture through which x-ray beam can pass. The sample may be also be a particulate solid (e.g., powder), a liquid or a gas—moving in the chamber or under pressure in the chamber, or exerting some other potentially disruptive forces or effects within the chamber. When irradiated by beam 24, at least one of the constituents of sample in chamber 16 typically is excited in such a fashion that the constituent x-ray fluoresces, that is, produces a secondary source of x-rays 26 due to excitation by x-rays 24. Again, since x-ray beam 26 is typically a diverging beam of x-rays, beam 26 is focused by means of the second x-ray focusing device 18, for example, a device similar to device 14, to produce a focused beam of x-rays 28 directed toward x-ray detector 20. It will be apparent to those of skill in the art that this and other aspects of the present invention, though described with respect to x-ray fluorescence applications, may also be utilized in x-ray diffraction, particle-beam, neutron or gamma ray applications.

X-ray detector 20 may be a proportional counter-type or a semiconductor type x-ray detector. Typically, x-ray detector 20 produces an electrical signal 30 containing at least some characteristic of the detected x-rays which is forwarded to an analyzer 32 for analysis, printout, or other display.

Figure 2:
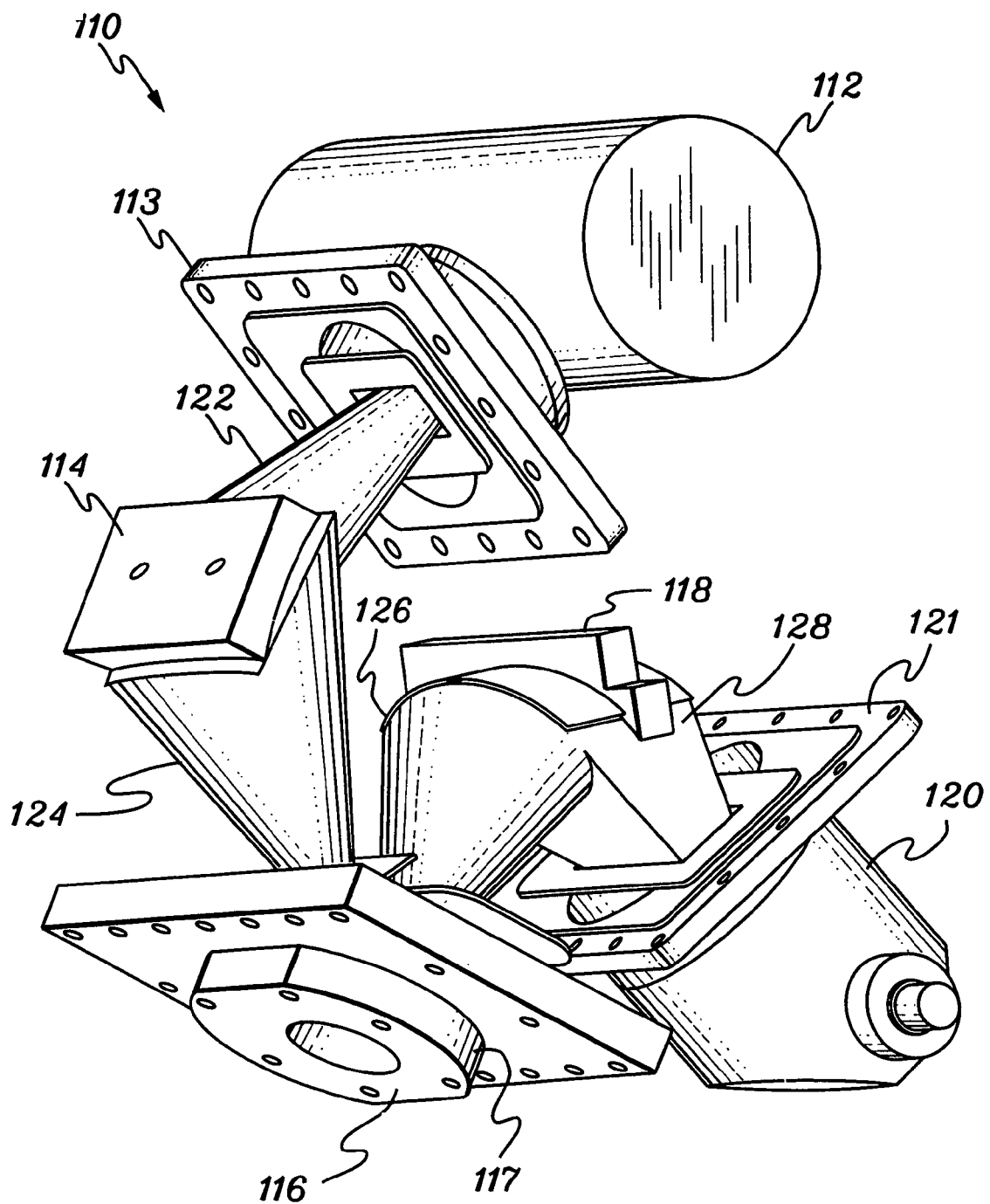
FIG. 2 is an isometric view of an exemplary x-ray fluorescence source/detection "engine" with an exemplary sample chamber.

FIG. 2 illustrates an x-ray fluorescence assembly 110 according to the above-incorporated U.S. patent application entitled "X-RAY TUBE AND METHOD AND APPARATUS FOR ANALYZING FLUID STREAMS USING X-RAYS" by Radley, et al. U.S. Ser. No. 60/336,584 filed Dec. 4, 2001. This is an example of a sulfur in fuels analysis system, and also employing the principles of monochromatic X-Ray excitation and collection as set forth in the above-incorporated U.S. patent application entitled XRF SYSTEM INCLUDING FOCUSING OPTIC ON EXCITATION SIDE AND MONOCHROMATIC COLLECTION by Chen, et al. U.S. Ser. No. 60/299,371 filed Jun. 19, 2001. X-ray fluorescence assembly 110 (shown with its housing removed) comprises an x-ray source assembly 112, a conventional sample excitation chamber assembly 116 and an x-ray detector assembly 120. A curved crystal, focusing optic 114 is shown in the excitation path, along with another curved crystal focusing optic 118 in the collection path. In a fashion analogous to the system 10 shown in FIG. 1, x-ray source assembly 112 produces an x-ray beam 122 which is focused by x-ray focusing optic 114 to produce a focused beam 124 on a sample under test in excitation chamber assembly 116. The x-ray fluorescence created by the x-ray irradiation of the sample in sample excitation chamber assembly 116 generates x-ray flourescent beam 126. Beam 126 is focused by x-ray focusing device 118 to provide a focused x-ray beam 128 which is directed to x-ray detector assembly 120. Source assembly 112, holder assembly 116, and detector assembly each include mounting flanges 113, 117, and 121, respectively for mounting each assembly to a housing (not shown).

For higher concentration levels XRF can be a useful technique for measuring composition, including measuring sulfur in fuels if the sulfur is at concentrations higher than 30-100 ppm, depending on different instrument approaches. But, some of the incident x-rays scatter, producing an unavoidable background. This is why conventional XRF requires certain improvements to be used for trace amounts of sulfur in fuels. In these conventional XRF methods (again, for example, the D2622 method) excitation of the sample is practiced using polychromatic x-rays. Among other things, the use of polychromatic x-ray excitation requires the use of at least two x-ray wavelengths to correct for errors inherent in polychromatic excitation. Excitation, by means of x-ray focusing and monochromating device 114, produces monochromatic x-rays. The use of monochromatic excitation avoids the need to correct detection errors which is typically required when using polychromatic excitation. For example, background radiation levels are reduced since there is no Bremsstrahlung illumination. As a result, such a system provides a higher signal to noise ratio than prior art methods using polychromatic excitation.

Energy dispersive XRF (EDXRF) uses a wavelength sensitive detector. These detectors can determine the wavelength of the incident x rays. But the detectors have to be cooled, some by liquid nitrogen, to have sufficient resolution. Wavelength dispersive XRF (WDXRF) uses a collecting monochromator 118, typically either flat or singly curved. The monochromator collects and passes a single wavelength. Then the detector only needs to be an x-ray counter. The detector does not need to distinguish the wavelength which is done by the monochromator. WDXRF is useful if elements in the sample with characteristic lines that are so close that the resolution of EDXRF is not enough to separate them. This can be the case with other elements present in fuels, such as lead which interferes with the sulfur characteristic line.

In prior art methods of XRF detection, for example, in the D2622 method, the sample excitation path and detection path are maintained in an inert gas atmosphere, for example, in a helium atmosphere. However, the availability of inert gases, especially in remote locations, makes the implementation of these prior art processes inconvenient. In contrast, here the sample excitation path and the detection path may be maintained under vacuum and no inert gas is necessary. For example, the radiation paths of system 110 shown in FIG. 2 may be held under vacuum, for example, at least about 15 torr. The vacuum can be provided by a venturi pump having no moving parts. However, if desired available, an inert gas such as nitrogen or helium can be introduced and maintained in a housing, for example, under pressure.

The use of a vacuum enclosing the x-ray engine (e.g., source, excitation path, collection path, and detector) leads to certain problems at the sample interface—at the respective focal spots of beams 124 and 126. In FIG. 2, the engine's interface to the sample chamber 116 is not directly shown, but may consist of a beryllium (or other material) window—which is strong and has the requisite x-ray transparency. But, additional levels of transparency are required when the sample chamber and its operational environment present certain operational difficulties as discussed above, especially in on-line systems.

Figure 3:
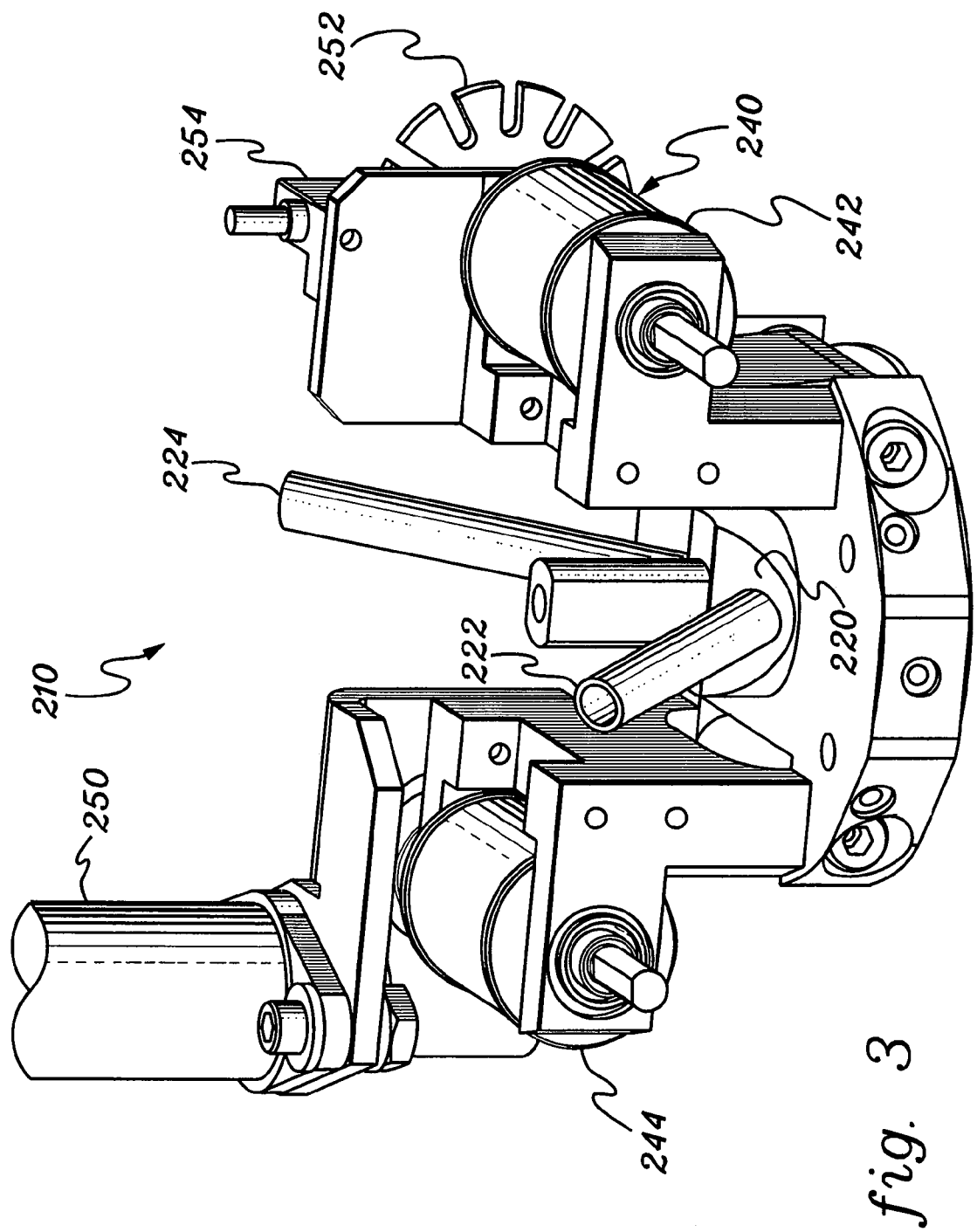
FIG. 3 is an isometric, solid view of a sample chamber apparatus in accordance with the present invention.
Figure 4:
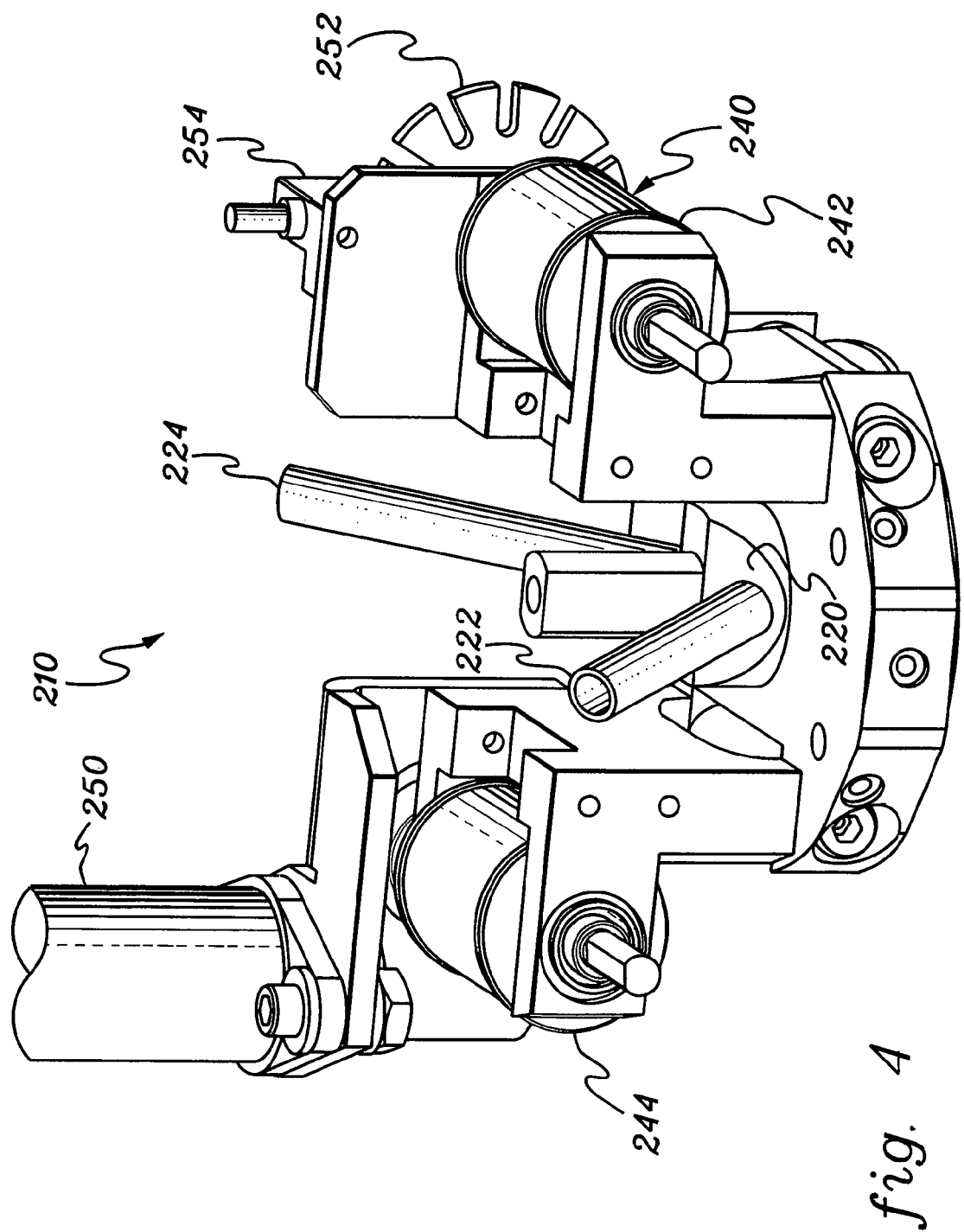
FIG. 4 is a line drawing of the apparatus of FIG. 3.
Figure 5:
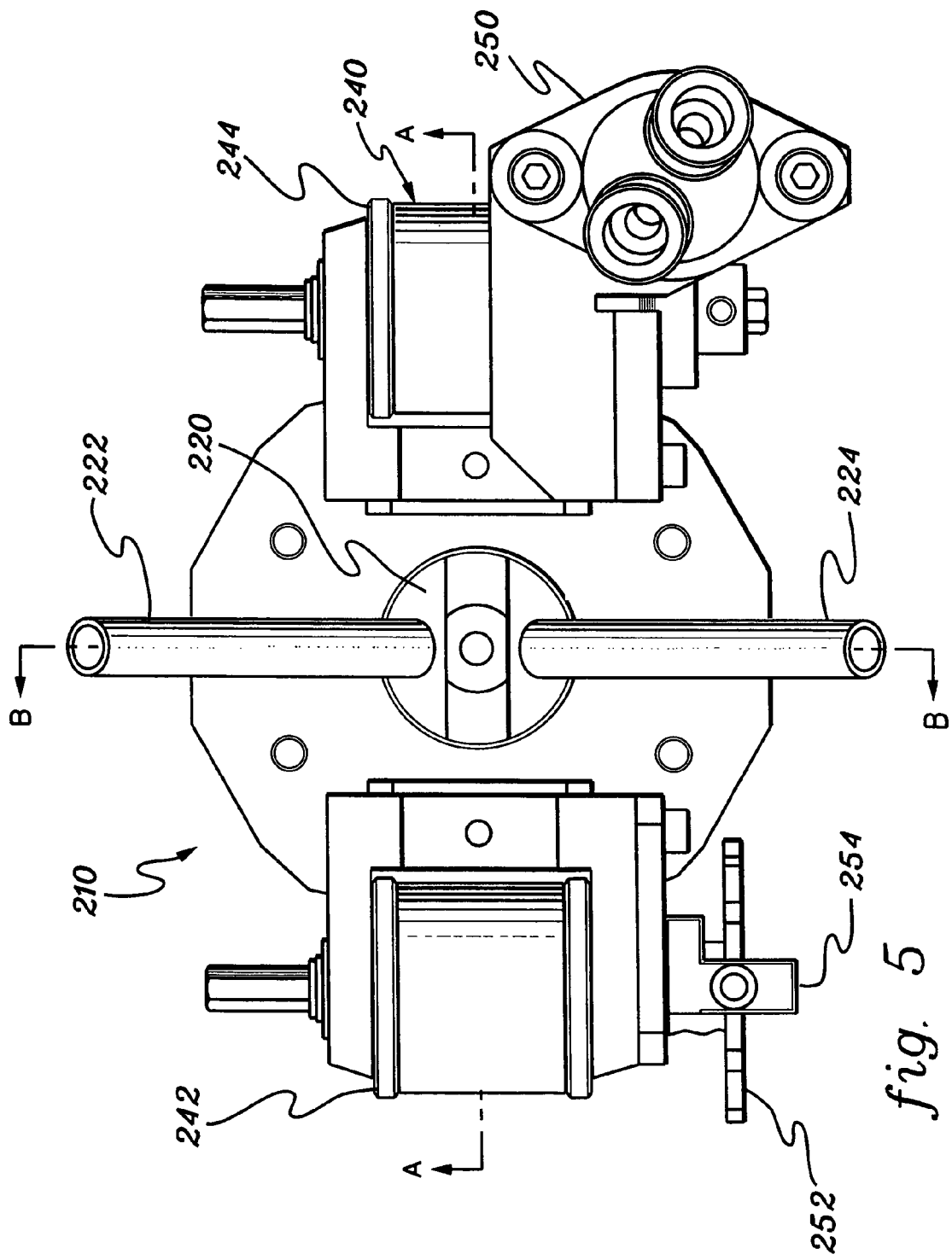
FIG. 5 is a top view of the apparatus of FIG. 4.

In accordance with the present invention, and with reference to FIGS. 3-5 (where like numerals are used to refer to like elements), an improved sample handling apparatus 210 is shown particularly suited to handle certain adverse conditions characteristic of on-line systems. The apparatus includes a sample chamber 220 having input 222 and output 224 sample ports for, e.g., particulate, liquid or gas moving through the system under pressure and requiring measurement. The apparatus includes a moveable barrier film 240 wound around a feed reel 242 and a take-up reel 244. The film, as discussed further below, runs past a sample aperture in a cavity at the bottom face of the chamber 220 (in fluid communication with the input and output ports) and provides an x-ray transparent barrier between the sample chamber and the x-ray engine 110 discussed above. The improved sample handling apparatus is thus designed to replace the apparatus conventional sample chamber 116 discussed above. The barrier maintains compatibility with the environment from which the sample is drawn (e.g., pressurized) while maintaining the integrity of the x-ray engine, possibly itself under a vacuum.

In the embodiment shown, the take-up reel can be driven by a remotely-controlled motor 250 to move the film past a sample aperture at the bottom face of the chamber. A trigger wheel 252 and photo-electric sensor 254 can be used to remotely sense and report the amount of movement—using standard connections to a computer network (not shown). In this exemplary embodiment, the barrier movement is not envisioned to be a continuous movement during sample measurement, rather, is envisioned to either partially or fully "refresh" or "replace" areas of the barrier worn-out by adverse conditions, while maintaining the operating environments of both the x-ray engine 110 and the sample handling apparatus.

Figure 6A:
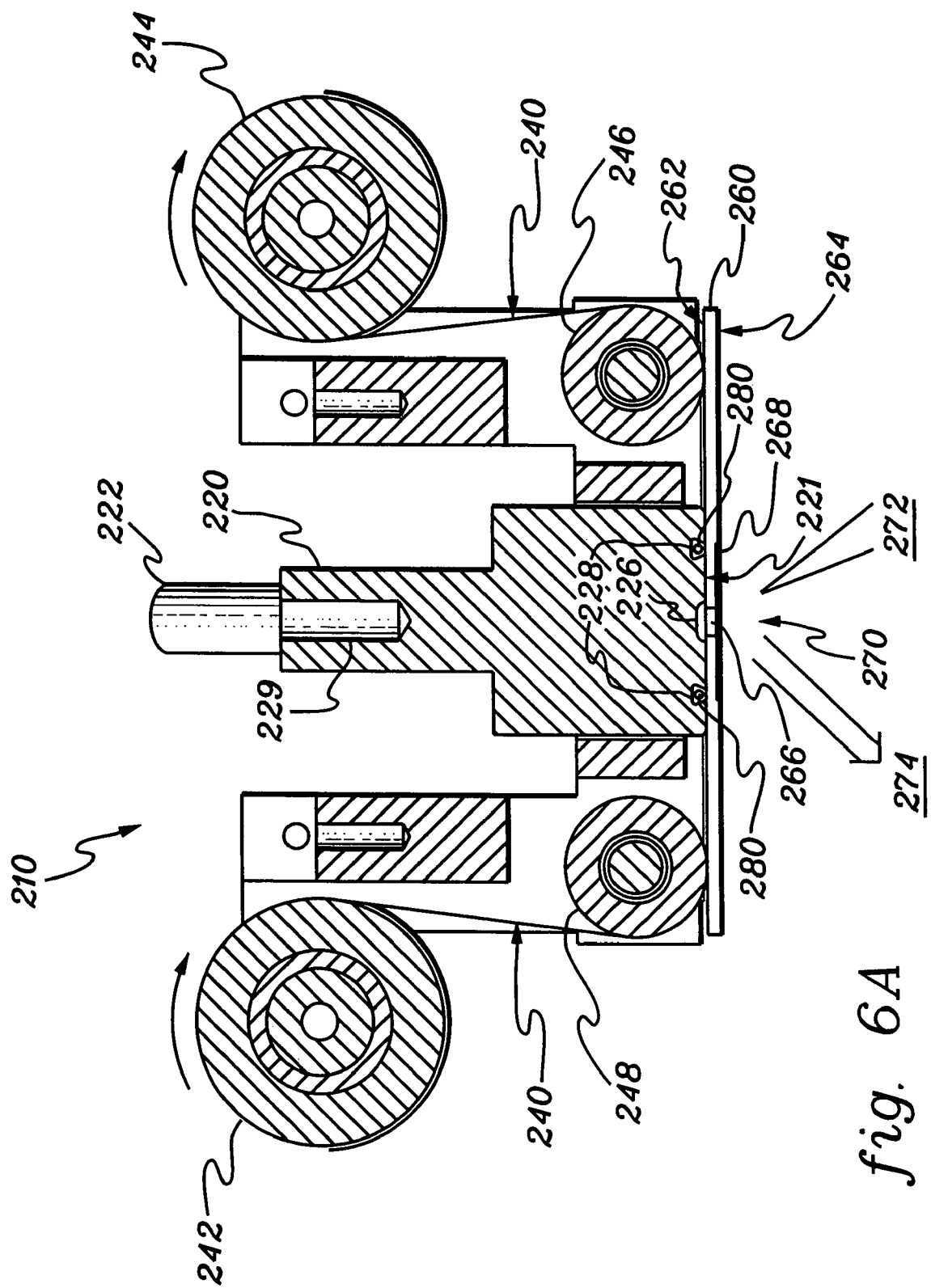
FIGS. 6A-6B are sectional views of the apparatus of FIGS. 3-5 taken along section AA.
Figure 6B:
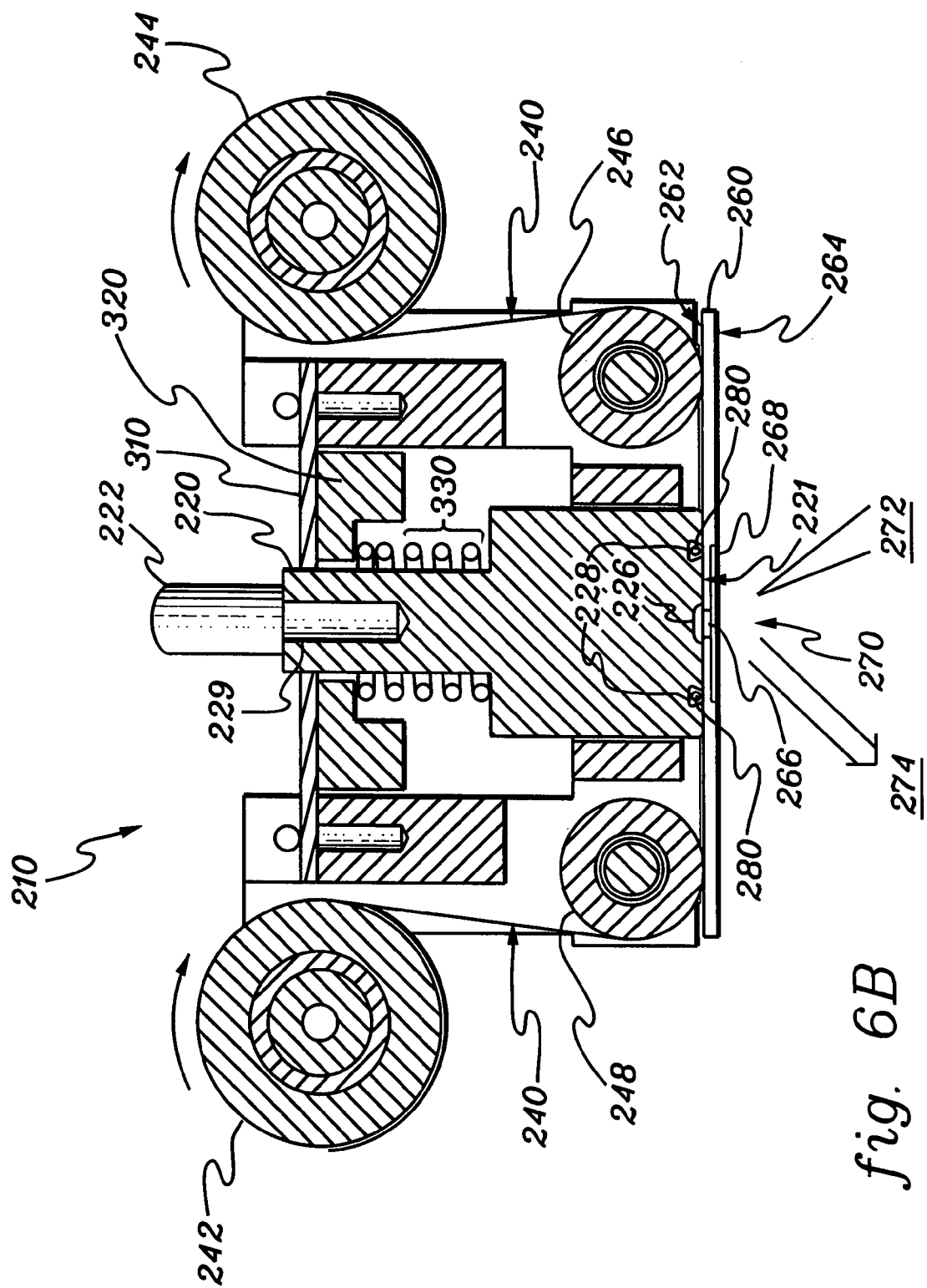

With reference to the sectional views of FIGS. 6 and 7 (where like numerals are used to refer to like components—and wherein FIG. 6B discloses certain improved embodiments of the invention discussed further below), feed reel 242 sources a supply of barrier film which runs along guide roller 248, and along the upper surface 262 of a sample window plate 260. (The bottom surface 264 of plate 260 faces the x-ray engine discussed above). The film, under tension, runs along the length of upper surface 262 and under sample chamber 220, toward a second guide roller 246 and then to take-up reel 244. The film is kept in proper tension throughout its path using the arrangement of guide rollers 246 and 248, an appropriate pressure on take-up reel 244, and a resistive pressure imposed on feed reel 242 by, for example, a slip clutch (not shown).

The most critical area requiring the barrier effect of film 240 is the radiation interface 270. This is the area where the incident x-ray energy 272 is focused toward a small spot of the sample in chamber 220 and from which the fluorescence 274 is captured. Here, a small feed through aperture 266 is formed through plate 260 to allow passage of the excitation and fluorescence radiation to the chamber 220. This aperture is about 2 mm in diameter in one embodiment and is subject to competing design concerns: A larger diameter is preferable to ease the flow of radiative energy used for the measurement—but a much smaller diameter is preferable to maintain the pressure of the sample. The aperture falls within a larger recess 268 formed into the bottom of plate 262 which enables a tighter interface to the beryllium window of the x-ray engine (not shown).

The sample is directed within chamber 220 toward its bottom surface 221. At the bottom surface, a sample cavity 226 is formed, in fluid communication with input port 222 and output port 224 and also aligned with the plate's aperture 266. This cavity forms the area subject to the x-ray energy through the plate's aperture 266. This is the critical point at which the barrier film is necessary. The cavity is part of the sample's path through the chamber, and therefore should be maintained at the same pressure as the sample—for example 20-100 psi or more—for compatibility in an on-line environment. The x-ray engine's vacuum environment cannot accommodate this pressure, nor can the small air interface 270 between the engine and the apparatus 210. Thus, in accordance with the present invention, the bottom of sample cavity 226 is completely covered by the film 240 which is essentially "squeezed" between the upper surface 262 of plate 260 and bottom surface 221 of chamber 220.

The barrier film thus offers an x-ray-transparent boundary between the x-ray engine and the sample cavity 226. The sample cavity may be under pressure in a refinery or pipeline application, or may simply be handling caustic or corrosive materials (such as particulate matter) which tend to corrode this interface. Also, as discussed above, long-term exposure to x-rays causes sulfur adsorption on any window, possibly leaving residue which degrades the x-ray transparency of the window.

Therefore, in accordance with another aspect of the present invention, the barrier film is moveable to partially or fully refresh the portion thereof which was (before the movement) positioned between cavity 226 and aperture 266. This full or partial refresh allows a "clean" and therefore fully x-ray-transparent portion of the film to replace a worn portion thereof at this critical interface. This movement is effected using the reel/motor system discussed above.

While this barrier film movement is not generally envisioned to occur during sample measurement, it may nevertheless occur while the sample remains in the cavity 226 under pressure, or when sample pressure is relieved (possibly remotely using controllable pneumatic valves). In accordance with the present invention, a continuous groove 228 may be formed in the bottom surface 221 of the chamber around cavity 226. This groove is sized to hold an o-ring 280 or some other type of elastic material from which pressure can be released and reapplied, and the entire sample chamber can be moveably mounted in apparatus 210. O-ring can be formed of any suitable material such as Viton. The entire chamber 220 may move up and down vertically using a threaded piston/spring assembly 229, to apply and release pressure on the o-ring. As with the motor and sensor discussed above, this movement may also be remotely controlled. During sample measurement (but not during barrier film movement), full downward pressure can be applied to chamber 220 using a spring, compressing the o-ring and maintaining maximal pressure opposing the pressure in cavity 226, and also squeezing and holding film 240 in its proper operational position between cavity 226 and aperture 266. Maintaining this pressure will prevent unnecessary leakage of the sample into the system.

When movement of the barrier film is desired (e.g., at scheduled intervals or when measurements indicate possible corrosion or residue), the sample chamber 220 can be moved slightly upward, releasing enough pressure on the o-ring to allow the barrier film to be moved an appropriate distance with motor and take-up reel 244. In certain applications, sample pressure may be remotely relieved to ease this film movement and most if not all downward pressure can be removed from the o-ring. Alternatively, in an application where sample pressure must be maintained, the o-ring is kept at whatever pressure is necessary to keep the sample under its requisite pressure in cavity 226, while still allowing film movement.

Figure 8:
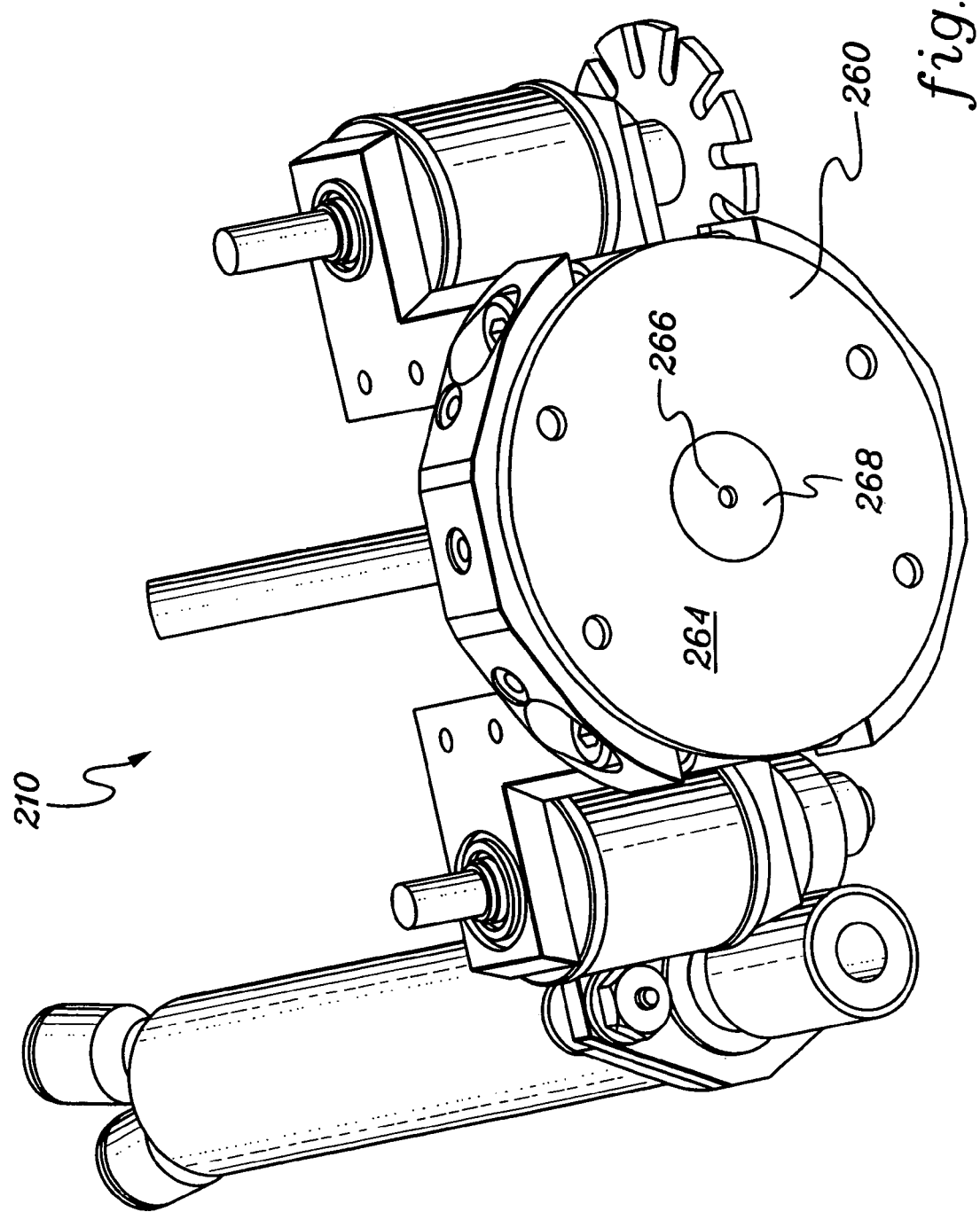
FIG. 8 is an isometric bottom view of the apparatus of FIGS. 3-5.

FIG. 8 is a bottom view of the assembly, illustrating the recess 268 and aperture 266 of plate 260.

Figure 9:
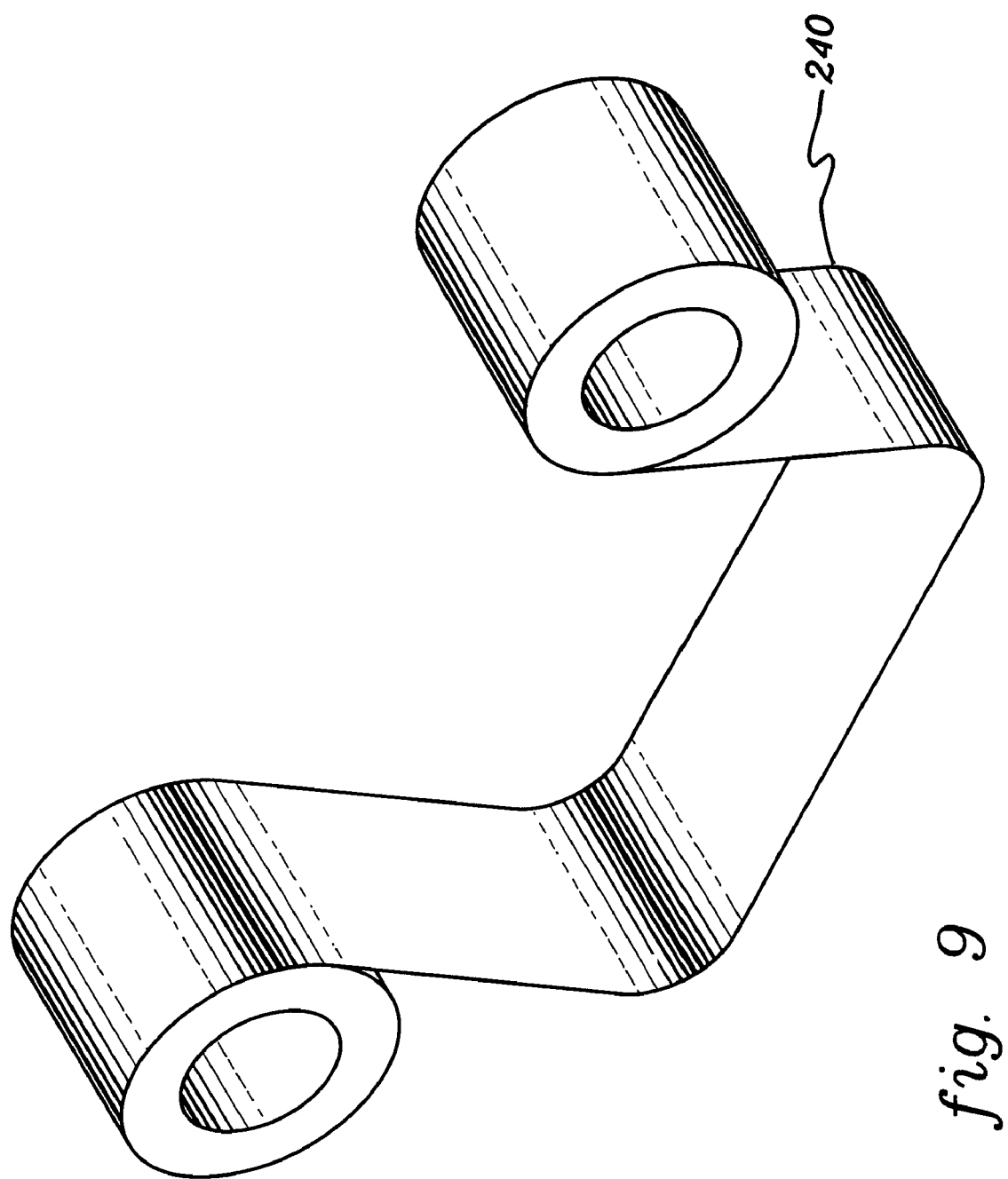
FIG. 9 is an isometric view of an exemplary moveable, x-ray transparent barrier film of the present invention shown arranged along the rolls and movement path shown in FIGS. 3-5.

FIG. 9 is an isometric view of only the moveable barrier film of the present invention arranged along the movement path discussed above. In one embodiment, the moveable film is formed of Kapton, which provides the requisite x-ray transparency, flexibility and tensile strength for this application (and resilience to fuel for the fuel applications discussed above). Other types of films are possible, such as mylar, etc.

The space budget at interface 270 must be carefully controlled to allow for effective x-ray excitation and collection of the sample in the cavity, but while also maintaining the proper vacuum or atmosphere in the engine and pressure of the sample—x-ray transparency. Therefore, plate 260 should be strong yet rather thin (e.g., 0.080 inches), as will the engine's beryllium window (e.g., 12.5 micron) and the barrier film (e.g., 7.5 microns). The spacing between the engine's window and the sample handling apparatus may be less than 2 mm. This space budget involves careful consideration of the excitation and collection focal spots, and also the amount of structural and material mass required to maintain the respective environments under pressure.

It will be understood that the present invention extends to a combined excitation/collection window as discussed above—or multiple such windows. Also, any relative movement between the sample's x-ray interface with a barrier is encompassed by the present invention—including a moving aperture into new portions of an otherwise static film.

The present invention accomplishes the objectives set forth above of an on-line, remotely controlled instrument: Transparency—it allows the transmission of x-rays with the minimum amount of x-ray absorption; strength—the barrier material is strong enough to support, e.g., fluid sample pressures of 20-100 psi or more from continuous flows in a pipeline; and finally, contamination control—movement of the barrier relative to the sample's x-ray interface addresses the potential, periodic contamination of the barrier from the sample material and/or the measurement environment.

Certain improved embodiments of the present invention are now described with reference to FIG. 6B (where like numerals are used to designate like elements from FIG. 6A). An anti-friction coating can be used on surface 262 of plate 260 to facilitate movement of the barrier across this plate during the refresh cycle discussed above. Cavity 226 can be sized to reduce any background radiation fluorescing off of its walls, e.g., can be sized larger than the size shown. In another embodiment, a coil spring 330 (or similar pressure-applying technique, e.g., leaf spring, pneumatic, hydraulic, foam, etc.) can be added to establish a constant, predictable downward pressure on o-ring 280 and barrier 240. Spring 330, held by guide 320, applies downward pressure to chamber housing 220 from the fixed plate 310 which is affixed to the outer (stationary) body of apparatus 210. When chamber 220 is in its "up"/relief position as discussed above, the spring 330 (sized according to the pressure required) provides a consistent level of pressure on both the o-ring and the barrier. With this pre-determined pressure level provided by the separate spring, the chamber movement mechanism need not be controlled to provide this precise level of pressure required to maintain o-ring seal while still allowing film movement. This consistent downward pressure enhances the operational predictability and overall reliability of the apparatus, especially the o-ring and barrier.

While the invention has been particularly shown and described with reference to preferred embodiment, it will be understood by those skilled in the art that various changes in form and details may be made to the invention without departing from the spirit and scope of the invention described in the following claims.

What is claimed is:

1. An apparatus for presenting a sample to a radiation interface of an analysis engine using x-ray, neutron ray, gamma ray or particle-beam radiation to analyze the sample, the apparatus comprising:
   a barrier, transparent to the radiation, and separating the sample from the engine, the barrier moveable relative to the radiation interface and over a sample cavity in which the sample is disposed;
   a barrier movement system to effect movement of said barrier;
   a sample chamber having a surface into which the sample cavity is formed;
   an opposition surface opposing the sample cavity having an aperture allowing passage of the radiation to and from the sample cavity,
      wherein the barrier is disposed between the surface of the sample chamber and the opposition surface, and
      wherein the sample chamber is moveable relative to the opposition surface to increase and decrease pressure on the barrier; and
   an elastic material disposed between the sample chamber and the opposition surface, and around the sample cavity, to prevent unnecessary leakage of the sample;
   wherein the barrier maintains the sample in the sample cavity during analysis of the sample by the analysis engine, and wherein the pressure on the barrier can be decreased to allow movement of the barrier.

2. The apparatus of claim 1, wherein the barrier comprises a film, and wherein the barrier movement system comprises:
   a system of reels to provide and retrieve a generally continuous supply of film over said cavity.

3. The apparatus of claim 1, wherein the cavity forms a portion of a sample path through which the sample is moveable.

4. The apparatus of claim 3, wherein the sample is a liquid, the sample path comprises at least a portion of a pressurized pipeline through which the liquid is flowing, and the analysis engine performs a compositional analysis of the fluid while the liquid is flowing.

5. The apparatus of claim 4, wherein the liquid is a fuel and the compositional analysis comprises measuring the level of sulfur in said fuel.

6. The apparatus of claim 1, wherein the elastic material comprises an expandable ring.

7. The apparatus of claim 1, further comprising a spring or other pressure-applying device to provide consistent pressure on the elastic material when the barrier is being moved.

8. The apparatus of claim 1, wherein the opposition surface comprises a coating to reduce friction between the opposition surface and the barrier.

9. A method of presenting a sample to a radiation interface of an analysis engine using x-ray, neutron ray, gamma ray or particle-beam radiation to analyze the sample, the method comprising:
   moving a barrier relative to the interface and over a sample cavity in which the sample is disposed, the barrier transparent to the radiation and separating the sample from the engine, thereby providing a different portion of the barrier at said interface;
   pressurizing the sample cavity, wherein the barrier maintains the sample in the sample cavity during analysis of the sample by the analysis engine;
   providing a sample chamber having a surface into which the sample cavity is formed;

providing an opposition surface opposing the sample cavity having an aperture allowing passage of the radiation to and from the sample cavity;

disposing the barrier between the surface of the sample chamber and the opposition surface;

moving the sample chamber relative to the opposition surface to increase and decrease pressure on the barrier;

providing an elastic material between the sample chamber and the opposition surface, and around the sample cavity, to prevent unnecessary leakage of the sample; and decreasing pressure on the barrier during movement of the barrier to allow movement of the barrier.

10. The method of claim 9, wherein said moving includes providing and retrieving a generally continuous supply of film barrier over a sample cavity into which the sample is placed.

11. The method of claim 9, further comprising:
flowing the sample through the sample cavity.

12. The method of claim 11, wherein the sample cavity forms a portion of a sample path through which the sample is flowing.

13. The method of claim 12, wherein the sample is a liquid, the sample path comprises at least a portion of a pressurized pipeline through which the liquid is flowing, the method further comprising:

performing a compositional analysis of the fluid while the fluid is flowing.

14. The method of claim 13, wherein the liquid is a fuel and the compositional analysis comprises measuring the level of sulfur in said fuel.

15. The method of claim 9, wherein the elastic material comprises an expandable ring.

16. The method of claim 9, further comprising:
applying consistent pressure on the elastic material when the film is being moved, using a spring or other pressure-applying device.

17. The method of claim 9, wherein the opposition surface comprises a coating to reduce friction between the opposition surface and the film.

18. An apparatus for presenting a sample to a radiation interface of an analysis engine using x-ray, neutron ray, gamma ray or particle-beam radiation to analyze the sample, the apparatus comprising:

a barrier, transparent to the radiation, and separating the sample from the engine, the barrier moveable relative to the radiation interface;

a barrier movement system to effect movement of said barrier; and a focusing device in the engine which produces a focused beam of said radiation through the barrier, and toward said sample.

19. The apparatus of claim 18, wherein the barrier comprises a film movable over a cavity in which the sample is placed, and wherein the barrier movement system comprises:

a system of reels to provide and retrieve a generally continuous supply of film over said cavity.

20. The apparatus of claim 19, wherein the cavity forms a portion of a sample path through which the sample is moveable.

21. The apparatus of claim 20, wherein the sample path is pressurized and the film maintains the sample in said cavity.

22. The apparatus of claim 21, wherein the sample is a liquid, the sample path comprises at least a portion of a pressurized pipeline through which the liquid is flowing, and the analysis engine performs a compositional analysis of the fluid while the fluid is flowing.

23. The apparatus of claim 21, comprising:
a sample chamber having a surface into which the sample cavity is formed; and a plate opposing the sample cavity having an aperture allowing passage of the radiation to and from the sample cavity, wherein the film is disposed between the surface of the sample chamber and the plate, and wherein the sample chamber is moveable relative to the plate to increase and decrease pressure on the film.

24. The apparatus of claim 18, wherein the focusing device comprises at least one curved optic.

25. The apparatus of claim 24, wherein the curved optic comprises at least one doubly curved crystal optic.

26. The apparatus of claim 25, wherein the focusing device comprises capillary-type optic.

27. A method of presenting a sample to a radiation interface of an analysis engine using x-ray, neutron ray, gamma ray or particle-beam radiation to analyze the sample, the method comprising:

moving a barrier relative to the interface, the barrier transparent to the radiation and separating the sample from the engine, thereby providing a different portion of the barrier at said interface; and producing a focused beam of said radiation through the barrier, and toward said sample, using a focusing device.

28. The method of claim 27, wherein said moving includes providing and retrieving a generally continuous supply of film barrier over a sample cavity into which the sample is placed.

29. The method of claim 28, further comprising:
flowing the sample through the sample cavity.

30. The method of claim 29, wherein the sample cavity forms a portion of a sample path through which the sample is flowing.

31. The method of claim 30, wherein said flowing comprises:

pressurizing the sample path, wherein the film maintains the sample in the cavity during analysis of the sample by the analysis engine.

32. The method of claim 31, wherein the sample is a liquid, the sample path comprises at least a portion of a pressurized pipeline through which the liquid is flowing, the method further comprising:

performing a compositional analysis of the fluid while the fluid is flowing.

33. The method of claim 31, comprising:
providing a sample chamber having a surface into which the sample cavity is formed; and providing a plate opposing the sample cavity having an aperture allowing passage of the radiation to and from the sample cavity, disposing the film between the surface of the sample chamber and the plate, and moving the sample chamber relative to the plate to increase and decrease pressure on the film.

34. The method of claim 27, wherein the focusing device comprises at least one curved optic.

35. The method of claim 34, wherein the curved optic comprises at least one doubly curved crystal optic.

36. The method of claim 27, wherein the focusing device comprises capillary-type optic.

* * * * *